US008065002B2

(12) United States Patent
Arand et al.

(10) Patent No.: US 8,065,002 B2
(45) Date of Patent: Nov. 22, 2011

(54) PACEMAKER-PATIENT HEMODYNAMIC ASSESSMENT/ADJUSTMENT METHODOLOGY

(75) Inventors: Patricia A. Arand, McMinnville, OR (US); Peter T. Bauer, West Linn, OR (US); Robert A. Warner, Tigard, OR (US)

(73) Assignee: Inovise Medical, Inc., Portland, OR (US)

( * ) Notice: Subject to any disclaimer, the term of this patent is extended or adjusted under 35 U.S.C. 154(b) by 760 days.

(21) Appl. No.: 12/148,214

(22) Filed: Apr. 16, 2008

(65) Prior Publication Data
US 2008/0195164 A1 Aug. 14, 2008

Related U.S. Application Data

(62) Division of application No. 11/264,328, filed on Nov. 1, 2005, now abandoned.

(60) Provisional application No. 60/644,501, filed on Jan. 12, 2005.

(51) Int. Cl.
A61N 1/37 (2006.01)
(52) U.S. Cl. ........... 607/17; 600/513; 600/519; 600/528
(58) Field of Classification Search .................. 600/508, 600/509, 513, 514, 519, 528
See application file for complete search history.

(56) References Cited

U.S. PATENT DOCUMENTS

| 5,392,780 | A | 2/1995 | Ogino et al. |
| 7,174,203 | B2 | 2/2007 | Arand et al. |
| 7,225,021 | B1 | 5/2007 | Park et al. |
| 7,559,903 | B2 | 7/2009 | Moussavi et al. |
| 2005/0010254 | A1* | 1/2005 | Zhang et al. ............... 607/9 |
| 2005/0027323 | A1 | 2/2005 | Mulligan et al. |
| 2008/0021510 | A1 | 1/2008 | Mi et al. |
| 2008/0177191 | A1 | 7/2008 | Patangay et al. |
| 2009/0165559 | A1 | 7/2009 | Lec |

OTHER PUBLICATIONS

International Search Report, Serial No. PCT/US10/055696, dated Dec. 23, 2010, 13 pages total.
USPTO Office Action, U.S. Appl. No. 12/315,165, dated Nov. 12, 2010, 9 pages total.
USPTO Office Action, U.S. Appl. No. 11/264,328, dated May 9, 2008, 7 pages total.
USPTO Office Action, U.S. Appl. No. 11/264,328, dated Oct. 16, 2008, 8 pages total.

* cited by examiner

Primary Examiner — Scott Getzow
Assistant Examiner — Joseph Dietrich
(74) Attorney, Agent, or Firm — John M. Dickinson, Esq.; Robert D. Varitz, Esq.

(57) ABSTRACT

A method for gathering, creating and utilizing signal-processed ECG and acoustic signals for assessing, via presenting a highly intuitive, multi-component, common-time-base, real-time output display of selected (1) timing, (2) relative timing, and (3) other significant heart-behavioral elements relevant to such an assessment, a pacemaker patient's hemodynamic condition. The method offers an important option and capability for automatic, and/or manual, medical-treatment and/or pacemaker-control feedback, in real time, to improve a pacemaker patient's hemodynamic status, with such a patient's resulting hemodynamic-behavioral/status changes caused by such feedback being viewable immediately in the invention's produced output display.

8 Claims, 6 Drawing Sheets

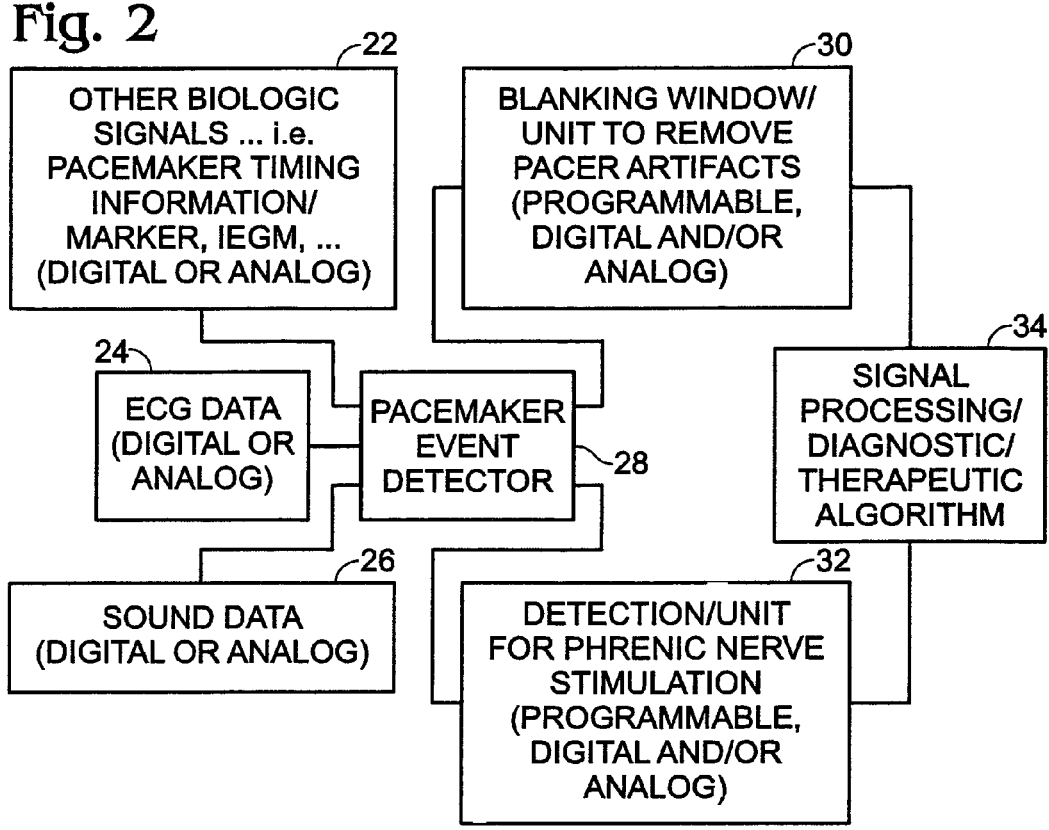
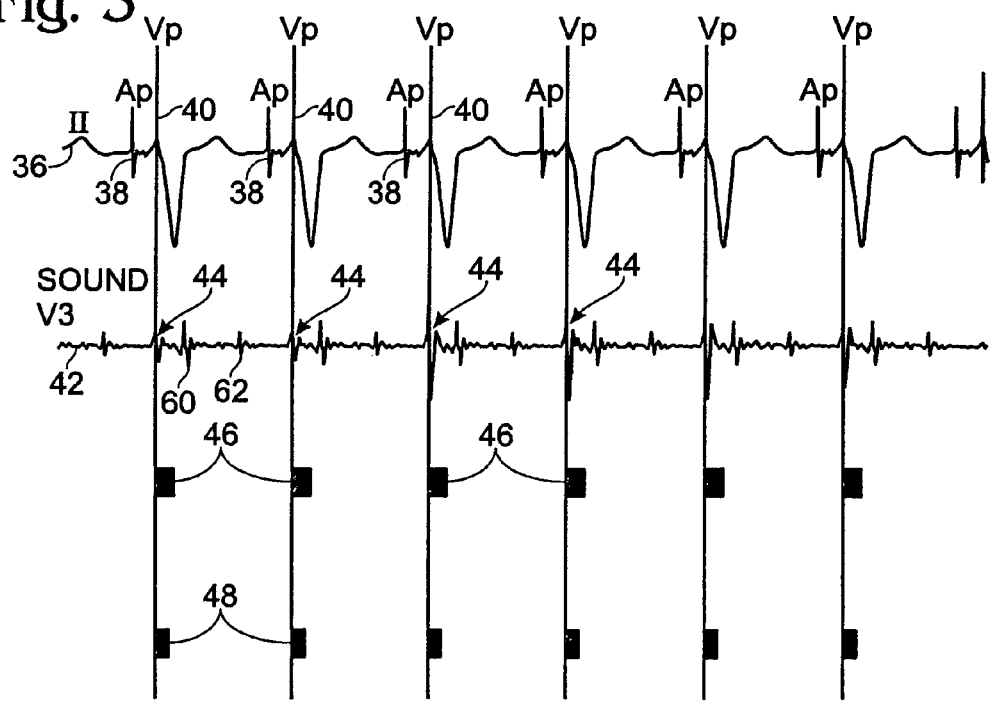

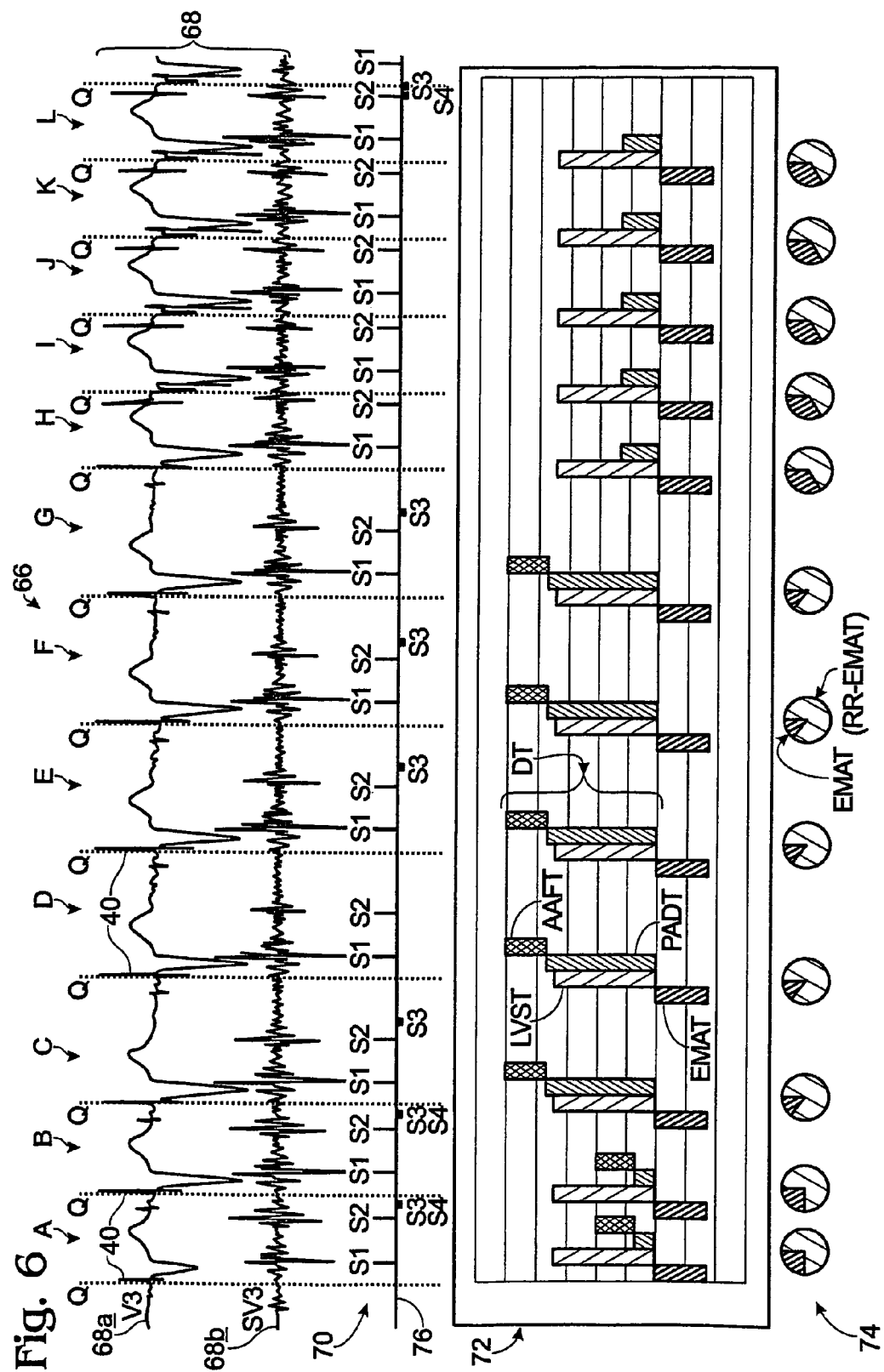

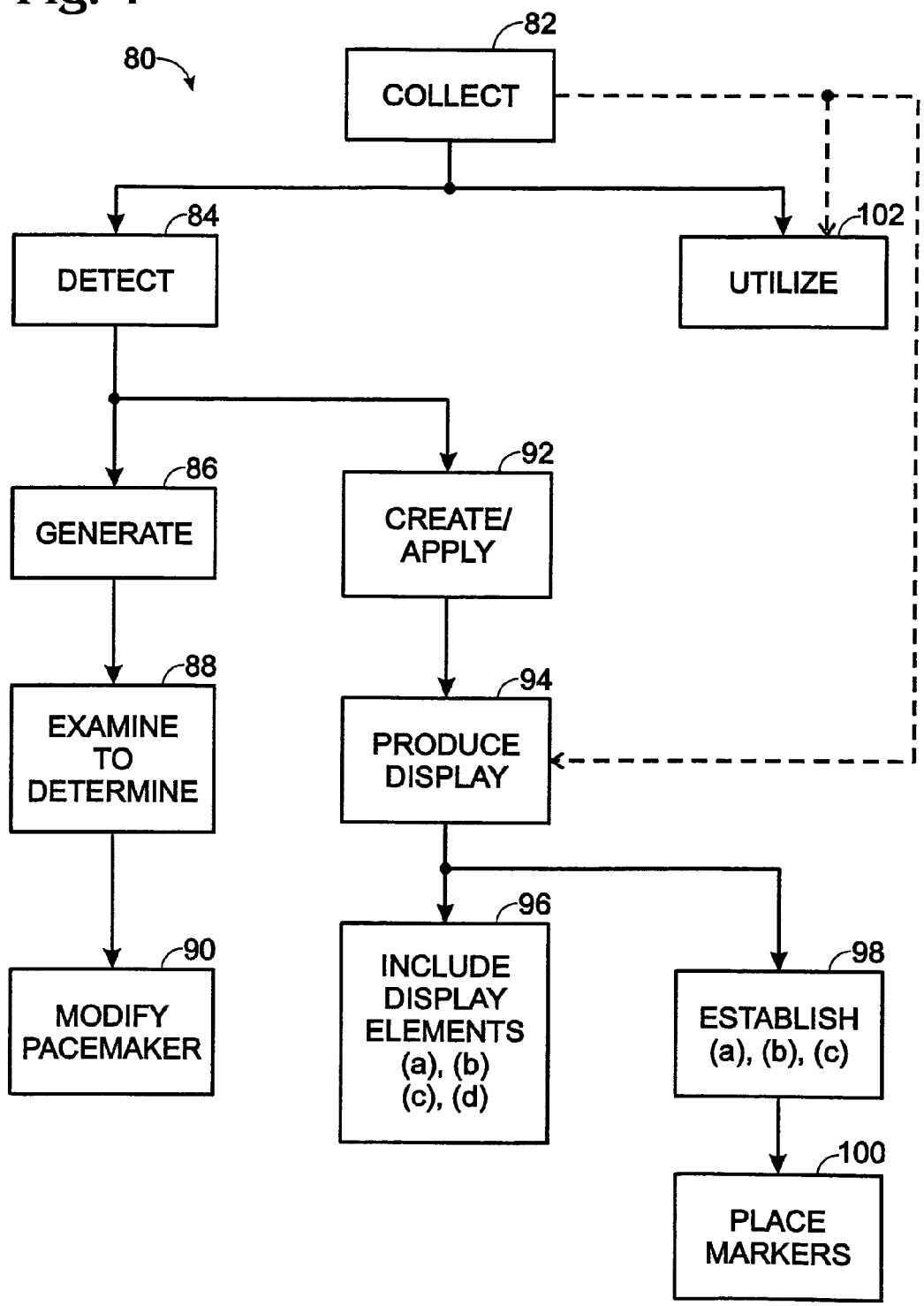

PACEMAKER-PATIENT HEMODYNAMIC ASSESSMENT/ADJUSTMENT METHODOLOGY

CROSS REFERENCES TO RELATED APPLICATIONS

This application is a Division of U.S. patent application Ser. No. 11/264,328, filed Nov. 1, 2005, for "Hemodynamic Assessment/Adjustment" (now abandoned), which claims priority to the filing date of U.S. Provisional Patent Application Ser. No. 60/644,501, filed Jan. 12, 2005, for "Methodology and Apparatus for Cooperative, Interrelated ECG-Sound and Pacemaker Heart-Activity, and Associated Signal, Interaction". The entire disclosure contents of these two, prior-filed patent applications are hereby incorporated herein by reference.

BACKGROUND AND SUMMARY OF THE INVENTION

This invention pertains to a certain aspect of cardiology, and in particular, to methodology and associated system apparatus that are employable with respect to pacemaker patients to obtain useful heart-sound and ECG-electrical information which enables a very accurate, and graphically intuitive, assessment of a patient's hemodynamic status. The invention also provides an important feedback opportunity for adjusting such a patient's current medical treatment, including the making of a pacemaker operational adjustment, in a manner aimed at improving that patient's hemodynamic condition. With the system and methodology of the invention in operation, the results of such feedback can be viewed immediately in real time.

The invention thus addresses an important area of cardiology wherein it is considered to be very useful and important to be able, under real-time, result-observation conditions, to fine-tune a pacemaker-patient's hemodynamic behavior and condition. The terms "pacemaker" and "pacemaker patient" are employed herein in relation to patients and implant equipment involving cardiac resynchronization therapy.

In this context, it is now very well recognized that, in addition to the heart-condition-assessment value of possessing accurately gathered and clearly readable ECG electrical information, is also extremely valuable to obtain, for accurate viewing, simultaneously occurring heart-sound information relating especially to the heart sounds known as the $S_1$, $S_2$, $S_3$ and $S_4$ heart sounds. As those skilled in the art recognize, there are various kinds of conditions which can make difficult the accurate acquisition and identification of clearly confirmable heart sounds, often because of various "other conditions" which tend to obscure accurate heart-sound information. One of these troublesome, "obscuring" conditions exhibits itself sometimes in the presence of pacemaker operation in the form of phrenic nerve stimulation. More specifically, too vigorous a pacemaker ventricular pacing pulse, an issue in and of itself, can produce such stimulation which, in turn generates an acoustic artifact that can "confuse" a heart-sound diagnostic algorithm in a way which mars accurate heart-sound investigation.

The present invention, in the context of improving heart-sound collection and display for hemodynamic status assessment and adjustment in the realm of pacemaker operation, takes particular aim at this circumstance and these issues—namely, at the above-mentioned, unwanted events involving a subject whose heart has been equipped with a pacemaker. It does so, as will be seen, with unique methodology which leads to very accurate and reliable gathering and intuitive presentation of both ECG-electrical and heart-sound acoustic information, with appropriate processing being applied to the gathered information to assure a high level of certainty regarding acquired audio data containing heart-sound information in categories that are important to the assessment and management of a subject's hemodynamic condition. This presentation capability of the invention is, as will be seen, extremely useful in the world of pacemaker patients.

Describing features of the invention in the subject "pacemaker" setting, the present invention operates to recognize potential "phrenic nerve stimulation" problems, and as such, provides signal-collection and signal-processing circuitry operation and methodology which responds to real time pacemaker operation in a manner that effectively (a) prevents the mentioned heart-sound confusion issue from surfacing, (b) informs a physician, clinician, etc. that a pacemaker's ventricular pacing pulse may need to be adjusted, and (c) opens a significant door for the improved gathering and processing accuracy, and the presentation, of heart-sound information leading to accurate assessment (indeed "picturing") of a subject's hemodynamic condition.

Additionally, the invention addresses the utility of employing such carefully gathered and processed information in a manner enabling feedback control to be applied to an operating pacemaker so as to enable the physician, or other party, (working with a particular pacemaker subject) to fine-tune the interrelated operations of the subject's heart and the associated pacemaker so as to improve that subject's hemodynamic condition.

As an important aside feature, medical treatment feedback, other than that relating to pacemaker operation, is also encouraged, promoted, and made available, based on operation of the invention, for improving, and for observing feedback results in real time regarding, a patient's hemodynamic condition.

The invention further features the creation of a unique, visual, graphical presentation (with geometric elements) of gathered ECG-electrical and heart-sound acoustic information, in a real time manner, and in such as fashion that the employment of feedback to control various medical treatment and/or pacemaker operations so as to improve hemodynamic behavior can be seen immediately on a very intuitive visual representation of the associated subject's actual, then-existent, hemodynamic condition and behavior.

These and various other features and advantages which are offered by the present invention will become more fully apparent as the description which now follows is read in conjunction with the accompanying drawings.

DESCRIPTION OF THE DRAWINGS

FIG. 2 is a block/schematic diagram labeled to illustrate detection of pacemaker-triggered phrenic nerve stimulation, and the creation of a special sound-information blanking window to eliminate unwanted and confusion-prone processing of any acoustic artifact created by such stimulation.

FIG. 3 provides a graphical illustration which relates to the operation of what is shown in FIG. 2.

FIG. 6 is a multi-component graphic illustration derived from information gathered in accordance with practice of the present invention to furnish an intuitive display, over a period of time including about one-dozen cardiac cycles, of a particular patient's (subject's) hemodynamic status. This figure, which has been prepared to show display output operation of the invention, specifically shows, among other things, an effect of pacemaker feedback control.

FIG. 7 is a high-level, block/schematic diagram illustrating the overall methodology of the present invention.

DETAILED DESCRIPTION OF THE INVENTION

Figure 1:
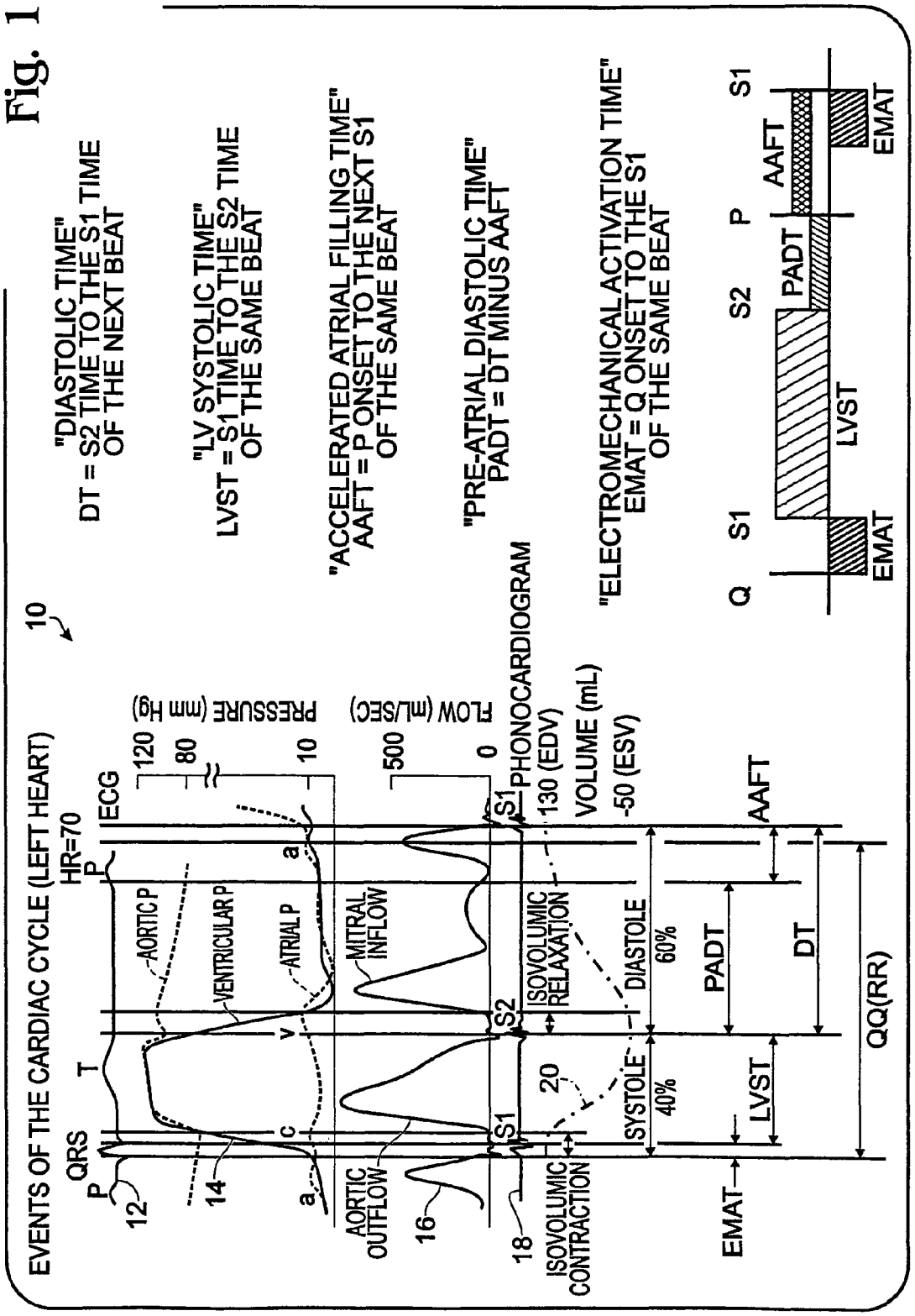
FIG. 1 provides a graphical illustration, well known to those skilled in the art, of a parameter legended illustration of the various basic events of the usual left heart cardiac cycle. This figure specifically carries labels of certain time intervals which are referenced in relation to what is shown in FIG. 6.

Turning now to the drawings, and referring first of all to FIG. 1, indicated generally at 10 is a relatively well known and conventional illustration of the events, and of certain measures of events, of a typical, single cardiac cycle with respect to the left side of the heart, referred to for simplicity purposes simply as the left heart. These events are those which normally take place, and are expected to take place, during such a cardiac cycle. At the lower portion of each of these two figures, certain timing intervals that are relevant in different ways to the practice of the present invention are specifically labeled by different clusters of capital letters. Set forth immediately below is a listing of the meanings of these letter labels:

AAFT—Accelerated Atrial Filling Time
DT—Diastolic Time
EMAT—Electromechanical Activation Time
LVST—L V Systolic Time
PADT—Pre-Atrial Diastolic Time
QQ(RR)—Interval between beats Still with reference to FIG. 1, this figure specifically shows a simple parameter model based on ECG/Sound timing intervals. These intervals are close approximations to hemodynamically relevant aspects of the cardiac cycle which can be extracted from echo, cardiac cath, ECG, and heart-sound measurements.

Looking at, and identifying, the graphical, time-based traces which appear on the left side of FIG. 1:

1. Top trace (12): ECG signal with makers for the p-wave (atrial depolarization), QRS complex (ventricular depolarization), and T-wave (ventricular re-polarization).
2. 2nd trace from top (14): Pressure tracings (obtainable through catheter measurements). Shown are the pressure curves for the left ventricle, the left atrium, and the aorta.
3. 3rd trace from top (16): Flow tracings (obtainable through echo tissue Doppler imaging (TDI)). When the pressure in the left ventricle is higher than in the aorta, blood is flowing into the aorta (happens between the S1 and S2 heart sounds)=aortic outflow; while the ventricular pressure is below the left atrial pressure, the left ventricle get filled with blood=mitral inflow. The mitral inflow occurs in three phases: a) passive filling (first hump between the S2 and the next S1)=Echo TDI E wave, b) diastasis (LA=LV pressure, small hump in the middle, hardly visible in Echo TDI), and c) active filling (atrial kick) while the left atrium contracts (hump just before the S1)=Echo TDI A-wave.
4. 4th trace from top (18): Heart sound trace showing an S1 (closure of mitral valve) and S2 (closure of aortic valve). The third heard sound is not shown, but it would occur toward the end of the E-wave in the flow trace.
5. 5th trace from top (20): Volume trace showing the changes in left ventricular volume from its minimum=ESV (end systolic volume, so the volume at the end of ventricular contraction) and its maximum=EDV (end diastolic volume, so the volume at the end of the ventricular filling phase).

As will be seen, it is the several specifically letter-labeled time periods appearing at the bottom of FIG. 1 which become employed in the intuitive output display which is shown in FIG. 6.

According to practice of the present invention, and in any suitable manner, during a common span of time, such as a time span which encompasses about a dozen successive cardiac cycles, simultaneous ECG-electrical and heart-sound acoustic signals are collected from anatomical contact sensors applied to the anatomy of a pacemaker patient, with that patient's, or subject's, pacemaker in full operation during this time interval.

In this setting, and as was generally mentioned above, one aspect of the present invention involves the capability of the methodology of the present invention accurately to obtain very useful ECG-electrical and heart-sound acoustic signals, with the latter basically "freed" from being "processed-confused" by any potentially troublesome pacemaker-induced acoustical artifact, such as a pacemaker-induced phrenic-nerve-stimulation artifact.

Another aspect of the invention involves, in relation to ECG-electrical and heart-sound acoustic data which is so gathered, and which is handled in a manner that avoids artifact disturbance, using that data in a feedback-loop manner to control various things, such as current medical treatment, and in the case of pacemaker involvement, various operating parameters and conditions of a subject's pacemaker, so as to improve the associated subject's hemodynamic status, and to do so in a fashion which can be observed immediately in real time as feedback information is employed, and as ECG-electrical and heart-sound acoustic signals continue to be simultaneously gathered and observed.

Still a further feature and aspect of the present invention involves the graphical presentation, as output information which is displayable on a screen, or on a printed strip chart, etc., in a manner which intuitively and quickly describes to a skilled observer various pieces of information which lead to an understanding of the relevant subject's hemodynamic condition.

Turning attention next to FIGS. 2 and 3 in the drawings, these two figures effectively illustrate that aspect of the present invention which relates to handling the issue of pacemaker-induced phrenic nerve stimulation. To those who are skilled in the relevant art, FIGS. 2 and 3, taken along with the related descriptive text which now follows, will fully explain the two special ways in which the present invention deals with such stimulation.

FIG. 2 includes seven blocks 22, 24, 26, 28, 30, 32, 34 which are interconnected functionally as shown by obvious interconnection lines. These blocks are labeled to indicate generally the function which they perform.

Block 22 represents methodology involved in collecting various electrically discernable biologic signal information, such as pacemaker timing and other information, which may be utilized directly or indirectly in the practice of this invention, either in cooperative addition to, or in some selectable ancillary manner with respect to, the gathering of heart-produced ECG-electrical signals and heart-sound acoustic signals which are sensed and collected, respectively, by blocks 24, 26. For example, certain pacemaker electrical activity, now to be discussed, may be collected for use in the practice of the present invention, either by block 22 or by block 24.

Blocks 22, 24, 26 collect their respective, associated signals from any suitable anatomical locations on a subject's body, with ECG-electrical signal information gathered from a classically recognizable anatomical site, such as the Lead II ECG anatomical site (as is represented in FIG. 3), and sound or acoustic information gathered from another recognized anatomical site, such as the V3 anatomical site (also represented in FIG. 3). These two, recognized anatomical sites are proximate one another, and, accordingly, ECG-electrical, and heart-sound acoustic signals may preferably be acquired essentially from the same, common site, and along a substantially common signal-collection axis.

Signals collected by blocks 22, 24, 26 are passed, in various ways to be explained, to signal-processing block 34, wherein one or more appropriate processing and diagnostic algorithms operate to create, ultimately, from acquired signal information, the useful output display information which is produced in accordance with practice of the present invention. Signals from these three blocks effectively pass "through" block 28, which performs pacemaker event detection functions that will be explained shortly, out of which block 28, acoustic signals, effectively en route to signal-processing block 34, are "sent" to that block either through a route including block 30, with respect to which a special acoustic blanking window is utilized in accordance with practice of the invention, or through block 32 wherein specific acoustic detection of phrenic nerve stimulation is detected, as will shortly be explained.

Those skilled in the relevant art will fully understand that there are various different ways in which the specific operations represented by blocks 22-34, inclusive, can be performed, and that, therefore, various specific signal-handling circuitry methodologic approaches, which may be entirely conventional in nature, may also be used. Accordingly, no specific details of the inner workings of these blocks are provided herein, inasmuch as they form no part of the present invention.

With respect to the operation of the present invention, electrical and acoustic signals which are gathered and handled in the fashion illustrated in FIG. 2 are collected in such a fashion as to focus upon ECG-electrical signals and heart-sound acoustic signals which can be processed for diagnostic purposes in a manner which does not allow the desired heart-sound acoustic signals to become confusingly treated by virtue of any phrenic nerve stimulation acoustic artifact that may be generated by operation of a subject's pacemaker. With specific reference to illustrative natures of signals that are collected and passed along essentially by blocks 24, 26 in FIG. 2, an ECG-electrical signal from Lead site II, collected by block 24, is shown generally at 36 in FIG. 3. Superimposed on this ECG-electrical signal, by virtue of the ongoing operation of a subject's pacemaker, are the usual atrial and ventricular electrical pacing pulses which are produced by the associated pacemaker, with atrial pulses Ap being shown generally at 38 in FIG. 3, and ventricular pacing pulses Vp being shown generally at 40 in FIG. 3.

An acoustic signal gathered by a block 26 in FIG. 2 is shown generally at 42 in FIG. 3, with there being superimposed on this acoustic signal an acoustic artifact 44 which results from the fact that ventricular pacing pulses 40 are energetic enough to be causing phrenic nerve stimulation.

It is with respect to the operation of block 28 in FIG. 2 that pacemaker events, such as ventricular pacing pulses 40, are detected to initiate certain important operations that are performed in the practice of the present invention.

According to one preferred practice of the present invention, under circumstances with a pacemaker operating with respect to a pacemaker patient, the appropriate ones of blocks 22, 24, 26 note and capture ECG-electrical signals, pacemaker atrial and ventricular pacing pulse electrical signals, and acoustic signals including heart-sound acoustic signals. In accordance with the intended operations of blocks 30, 32, on the occurrence of a ventricular pacing pulse, such as pulse 40, and in order to prevent the possibility of any phrenic nerve stimulation artifact triggered by that pulse becoming involved in the algorithmic signal-processing activity relating to discerning and correctly identifying heart-sound acoustical signals, block 30 creates what is referred to herein as a blanking time, or a blanking window, which begins at the onset of each pulse 40. These blanking times, or windows, are illustrated in FIG. 3 by the solid, darkened blocks which are shown at 46 in FIG. 3. While different specific time durations may be selected for establishing the length of each of these blanking windows, we have found that a blanking window which has a duration of about 30- to about 40-milliseconds is quite appropriate. These blanking windows prevent any acoustic-signal information from being furnished to signal-processing block 34 in a manner which would cause that information to become confused with anatomical acoustic signals that are intended to be gathered for the purpose of interpreting the presence of various heart sounds. In other words, this automatically triggered blanking window, triggered by the onset of a pacemaker's ventricular pacing pulse, prevents the likelihood that any phrenic nerve stimulation which produces an acoustic artifact will result in that artifact being confused by the signal-processing circuitry in block 34 with true heart-sound information.

As was mentioned, ventricular pacing pulses 40 as seen in FIG. 3 are energetic enough to be producing phrenic nerve stimulation at a level which produces related acoustic artifacts 44, and it is these artifacts which are blocked by the blanking time window from becoming confused with real heart-sound acoustical signals.

It is, however, important, and it is accommodated by operation of the present invention, that the event of phrenic nerve stimulation be made observable in some fashion to the physician, or clinician, etc., who is working with a patient whose data is being gathered, in order to determine whether the operation of the patient's pacemaker needs to be "toned down" to avoid such stimulation. Accordingly, a sound artifact 44, which is produced as illustrated in FIG. 3 by phrenic nerve stimulation triggered by pacemaker operation, is provided a special time window, i.e., it is "windowed" as illustrated by the darkened rectangles shown in FIG. 3 at 48. This windowing operation, furnished in accordance with the operation of block 32 in FIG. 2, provides information to the associated physician, clinician, etc., from which that person can determine whether or not an adjustment, in a feedback sense, manually or automatically provided, needs to be made in the operation of the pacemaker. The duration of each window 48 herein is about 30- to about 60-milliseconds.

Thus, insofar as the operation of the present invention is concerned and has been so far described, pacemaker ventricular pacing pulses trigger two kinds of windows, or intervals, one of which performs a blanking function to prevent any resulting sound artifacts derived from phrenic nerve stimulation from becoming confused in the analysis provided and produced for heart sounds, with the other window, at the same time, permitting any acoustic artifact which results from phrenic nerve stimulation to be noted so as to allow for immediate corrective adjustment, if necessary, of the pacing energy output by the associated pacemaker.

Control over pacemaker pulsing operation based upon observation of phrenic-nerve-stimulation-produced acoustic artifacts may, as suggested immediately above, preferably be performed by an attending clinician or physician, etc. but may also be handled in a computer-controlled automatic fashion, if so desired. Any such adjustment will, of course, become immediately "readable" with respect to its effect, as long as electrical and acoustic information continues to be gathered from the relevant subject.

Figure 4:
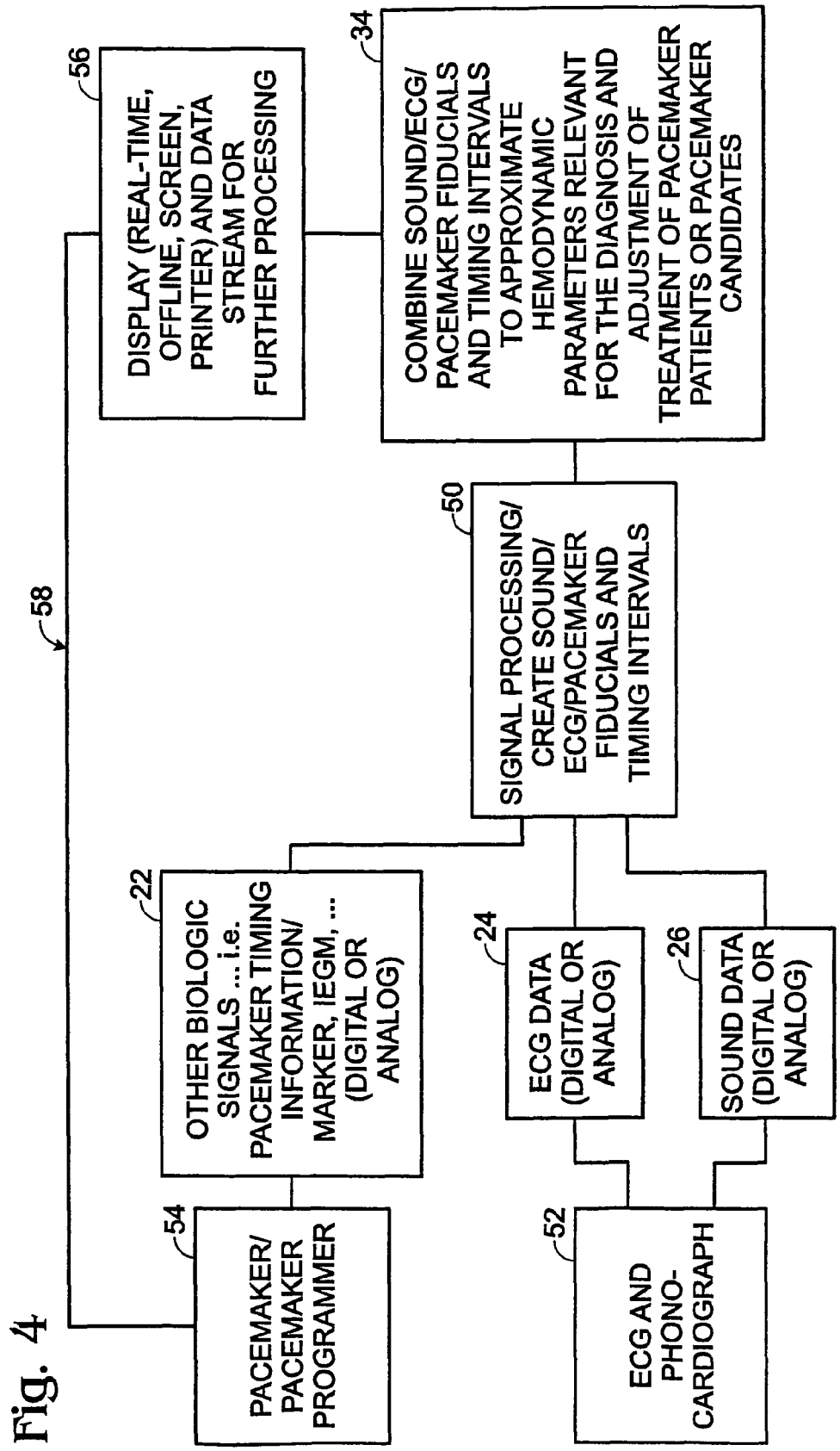
FIGS. 4 and 5 provide two different high-level block/schematic diagrams illustrating pacemaker control-feedback to improve subject hemodynamic status in accordance with practice of certain features of the present invention.
Figure 5:
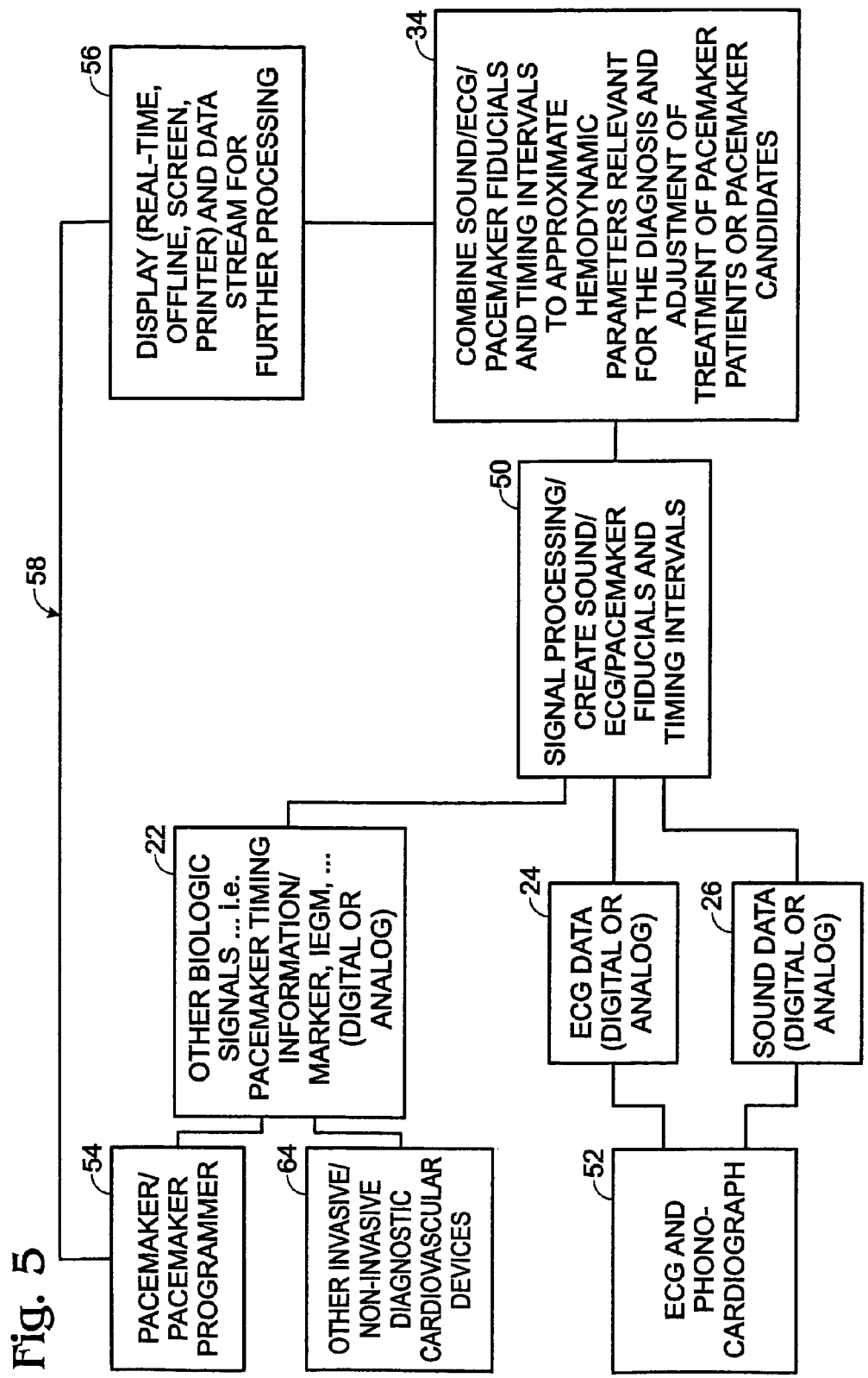

Turning attention now to FIGS. 4 and 5 in the drawings, here are provided two different block/schematic diagrams showing the methodology of the invention implemented in two, slightly different manners, all in accordance with practice of the present invention in the context of a pacemaker patient. These two drawing figures are seen to include visual representations of certain ones of the operational blocks which are also shown in, and described with respect to, FIG. 2. It will be soon be understood that the respective operations of the not-specifically-shown blocks (28. 30, 32) are carried out "within the confines" of certain other blocks which are specifically pictured in FIGS. 4 and 5.

FIG. 4, in addition to including blocks 22, 24, 26, 34, includes (a) a block 50 which is shown interposed blocks 22, 24, 26, and block 34, and which performs a certain amount of signal-processing with respect to marking and identifying various ECG and pacemaker fiducials and timing intervals, (b) a block 52 which generally represents anatomy-attachable ECG and acoustic sensors that feed data to blocks 24, 26, (c) a block 54 which represents a patient's pacemaker as well as access to the control circuitry for that pacemaker, and (d) a block 56 which plays a direct role in creating a visual output display on a display screen, or on a strip chart, etc., such as the display-screen display which is illustrated in FIG. 6 in the drawings.

A line 58 in FIG. 4 represents a feedback connection between block 56 and the pacemaker and its control circuitry 54. It should be understood that feedback information between block 56 and a pacemaker and its "controls" 54 may be implemented either automatically under appropriately programmed computer control, or manually. Such feedback is preferably performed during a data-gathering time with a patient, whereby the result(s) of information fed back to the pacemaker, in terms of how that feedback information affects pacemaker operation, and hence also affects a patient's hemodynamic behavior, can be observed rapidly in real time.

As will be more fully explained with respect to a description shortly to be given regarding FIG. 6 in the drawings, it should be apparent how a methodology organized in accordance with FIG. 4 operates in a "pacemaker" setting. To begin with, and recognizing that, effectively sitting within the "confines" of blocks 34, 50 in FIG. 4, are the functionalities afforded by blocks 28, 30, 32 in FIG. 2, blanking and windowing operations with respect to dealing with phrenic nerve stimulation are employed as described with respect to FIG. 2. Accordingly, no "artifact" audio information relating to phrenic nerve stimulation becomes confusingly processed with true heart-sound information, and yet a system operator is made immediately aware of any potential over-stimulation of the heart introduced by an overly energetic ventricular pacing pulse. Such awareness may be prompted in any suitable manner, as by a lighted warning element, a sound notification, or simply by an operator's attention being properly directed to a audio-signal trace which is provided in the output display generated by the invention. Referring back for a moment to FIG. 3 in the drawings, acoustic artifacts, such as artifact 44, thus do not enter the data stream which is being processed in block 34 to establish reliable heart-sound information, but are employed to enable pacemaker pacing control with respect to overly aggressive ventricular pacing pulses.

Other audio information, however, such as that information which is provided by pulses like those shown at 60, 62 in FIG. 3, is supplied for algorithmic processing for the purpose of non-confusingly and reliably noting and presenting information regarding true heart-sound acoustic data.

Through the operations of blocks 50, 34, 56 in FIG. 4, ECG-electrical, and proper heart-sound acoustic, information becomes processed (i.e., signal-processed) and presented in several very useful intuitive ways, as are illustrated in FIG. 6, and as will be discussed shortly herein.

FIG. 5 in the drawings is very similar to FIG. 4 as presented, except that this figure (5) shows an included block 64. This included block generally represents the fact that the methodology of this invention can readily accommodate the presence of other kinds (than pacemakers) of cardiovascular-related devices, such as cardiovascular diagnostic devices, both invasive, and noninvasive, with respect at least to the reception of useful diagnostic signals fed through block 22 into the system.

FIG. 6 in the drawings illustrates, generally at 66, a multi-component, highly intuitive, computer display-screen output display, produced by operation of the methodology of this invention. This display (which could also be presented in an output printing manner) has been generated, in terms of what is shown operationally in FIGS. 4 and 5, by blocks 56 therein.

Display 66 includes, generally speaking, (a) a graphical waveform portion 68 including two, vertically spaced traces 68a, 68b, (b) a time-based geometrical marker portion, or trace, 70, (c) a geometrical bar-graph portion, or trace, 72, and (d) a geometrical pie-chart portion, or trace, 74. Traces 70, 72, 74 are said herein to be keyed to information present in waveform traces 68a, 68b. In display 66, twelve successive cardiac cycles are shown, these being designated generally A, B, C, D, E, F, G, H, I, J, K, L. As can clearly be seen in FIG. 6, the events taking place within each of these twelve respective cardiac cycles, both electrically and sonically, are quite different from one another.

Trace 68a is an electrical waveform trace, which includes a blend of (1) ECG-electrical signals drawn directly from the classical V3 electrode Lead position on the anatomy, and (2) spike-like pulses 40 which are the same in character as pulses 40 illustrated in FIG. 3. These spike-like pulses, thus, represent a pacemaker's ventricular pacing pulses.

Trace 68b is an acoustic waveform trace which presents the acoustical information derived from the recognized V3 site on the anatomy.

Traces 68a, 68b, therefore, present a very clear time-related image of electrical and sound activity associated with the relevant subject's pacemaker-paced heart activity. These traces also provide, at a certain level, recognizable information relating to the subject patient's real time, current hemodynamic behavior (condition/status).

Trace 70 provides, projecting above and below a neutral axis line 76, intuitively displayed heart-sound markers which take the forms of upwardly and downwardly extending geometrical departures progressing from the datum of line 76. Those markers which extend above line 76 are related to systolically-associated heart-sound data, and those which extend below line 76, and which are represented by small, darkened rectangles, are related to diastolically-associated heart-sound signals.

In the particular display which is shown in FIG. 6, one can observe that heart sounds $S_1$ and $S_2$ provide the upwardly extending markers relative to line 76, and the $S_3$ and $S_4$ heart sounds are those which are illustrated extending below line 76. With respect to those marks which extend below line 76, and the fact that these are represented in FIG. 6 as small, darkened rectangles, it is contemplated that the aspect ratios of these rectangles may be "calibrated" to provide information such as heart-sound intensity and heart-sound frequency content.

In bar-graph trace 72, for each of the twelve different cardiac cycles illustrated in FIG. 6, there is presented a cluster of (geometrical) rectangles, with four such rectangles appearing in relation to the first seven cardiac cycles, and three-only such rectangles being presented with respect to the last five illustrated cardiac cycles. The particular block illustrations presented in FIG. 6 which are associated with cardiac cycle D have been labeled to relate the information contained by these rectangles to four of the interval measurements which are presented at the bottom of FIG. 1. Generally speaking, and with respect to the display approach illustrated in FIG. 6, the vertical dimensions of these rectangles represent duration times. The combined vertical dimensions of the blocks representing PADT and AAFT represent the DT time duration. This summing of the heights of the PADT and AAFT blocks is specifically illustrated in FIG. 6 with respect to the blocks that picture information contained in cardiac cycle E.

Further regarding what is shown in FIG. 6, it will be observed that cardiac cycles H-L, inclusive, represent a somewhat elevated heart rate as compared with what is shown in cardiac cycles A-G, inclusive. What one will also note is that, in the output information produced in accordance with the invention in trace 72 regarding these last five illustrated cardiac cycles, there is no rectangle shown which represents the value PADT. Among other things that a skilled observer learns from this particular intuitive display is that the associated subject's heart rate is so high that there is no ample time to permit pre-atrial diastolic time (PADT). This condition, of course, would dictate the need to make some adjustment in pacemaker operation, and very specifically an adjustment which slows down the subject's heart rate.

Looking for a moment especially at the presentation difference which exists in trace 72 with respect to cardiac cycles B and C, where, in cycle B, pre-atrial diastolic time (PADT) is quite small, and in cardiac cycle C, that same time is much larger, a comparison of these two presentations can be visualized as representing a change in the value of PADT which has been implemented through appropriate pacemaker feedback operation based upon the information presented in the bar graph block cluster which represents cardiac cycle B. It is thus the case that a physician, clinician, etc., working with a particular patient, can immediately observe, i.e., on a real time basis, whether such corrective feedback activity has produced an improvement in hemodynamic behavior. It will also be apparent that the blocks presented in bar graph portion 72 furnish a relatively high level of intuitive information respecting the associated subject's hemodynamic status, condition, or behavior.

Pie chart trace 74 presents, in recognizable, classical, geometrical pie-chart format, two important relatable time intervals, which are EMAT and (RR-EMAT). Those skilled in the art will understand that the proportional relationships between these two intervals as illustrated, for example, with respect to cardiac cycles D, E, F, and G represent a "better" hemodynamic patient status than, for example, do the pie-chart "proportional relationships" which are presented for cardiac cycles A, B, and H-L, inclusive.

Accordingly, one can readily see the substantial, intuitive-information-giving value of output information produced in accordance with practice of this invention as illustrated in FIG. 6.

Turning attention now to FIG. 7 in the drawings, here indicated at 80, in eleven blocks 82, 84, 86, 88, 90, 92, 94, 96, 98, 100, 102 is the flow architecture of the methodology of the present invention. This methodology, in high-level, general terms, takes the form of a method, utilizing signal-processed ECG-electrical and heart-sound acoustic signal information, for assessing a pacemaker patient's hemodynamic condition including the steps of: (1) collecting (block 82), over a selected time span, for transmission for hemodynamic-condition signal-processing, simultaneous ECG-electrical and heart-sound acoustic signals; (2) while so collecting, detecting, electrically, (block 84) pacemaker-induced ventricular stimulation; and (3) on detecting such stimulation, creating and applying (block 92) a selected blanking time which effectively prevents hemodynamic-condition signal-processing of acoustic signals that are collected during that blanking time.

In the practice of this methodology, and from a methodology-implementing systemic point of view, block 82 represents a sensor structure, block 84 a detecting structure, block 94 a signal-processing structure, and blocks 96, 98, 100 collectively, along with portions of block 94, a display structure.

Methodology 80 further includes the step of generating (block 86), substantially simultaneously with respect to the beginning of the created and applied blanking time, an acoustic window which permits examining (block 88) during that window, of any collected and thus windowed acoustic signal, in order to determine (block 88) whether that signal represents an acoustic artifact produced by pacemaker-induced phrenic nerve stimulation.

The method of the invention further includes the step of selectively using the determination of the presence of phrenic nerve stimulation to modify (block 90) the operation of a patient's pacemaker.

Further considering the methodology of the present invention, it includes, additionally, and in relation to the application of a blanking time, producing (block 94) a time-based graphical display containing indicia which are visually descriptive of selective components of the patient's hemodynamic condition. It is with respect to this producing step (block 94) that hemodynamic-condition signal-processing takes place, and thus the functions of previously mentioned blocks 50, 34, (and in part 56) can be visualized as taking place (in the context of FIG. 7) within block 94. This producing step includes establishing (block 98) (a) an ECG-signal display component, (b) a heart-sound acoustic signal display component, and (c) an intuitive, heart-sound marker display designating the time locations of at least one of heart sounds $S_1$, $S_2$, $S_3$ and $S_4$. Additionally, the step of establishing an intuitive heart-sound marker display includes placing therein (block 100) systolically-associated markers which are presented above a neutral axis line, and diastolically-associated sound markers which are displayed below the same neutral axis line.

In yet another manner of expressing a portion of the methodology of the invention, the display producing step (block 94) involves including in that display (block 96) elements relating to (a) electromechanical activation time, (b) LV systolic time, (c) pre-atrial diastolic time, and (d) accelerated atrial filling time.

One further way of visualizing the methodology of this invention is to recognize that it includes utilizing (block 102) collected ECG-electrical and heart-sound acoustic signals in a feedback manner to effect changes in the operation of a patient's pacemaker, and to do this in a fashion which is aimed at improving the patient's hemodynamic status.

Thus, a preferred methodology has been illustrated and described for this invention. This methodology, focused as it is on a pacemaker patient, features a unique approach (a) for collecting ECG-electrical and heart-sound acoustic anatomical signals, (b) for processing those signals in a manner whereby an event of pacemaker-induced phrenic nerve stimulation does not produce a condition of confusion with respect to heart-sound analysis, (c) for allowing information to be gathered whereby the vigor with respect to which a pacemaker applies pacing pulses can be adjusted, and (d) for producing, ultimately, results presentable in a highly intuitive output display that is readable easily by an expert to assess the current hemodynamic condition of a particular patient. As has been pointed out, the methodology of this invention also features the opportunity to apply feedback control information to a patient's pacemaker in a manner observable in real time with respect to the effect of a feedback adjustment, aimed at improving a patient's current hemodynamic status or condition.

In all implementations of the invention, medical treatment feedback (other than pacemaker-control feedback) based on what the display of the invention shows is possible, and can be viewed immediately in real time as to feedback result(s).

Thus, while the invention has been described in a certain manner herein with certain specific illustrations, it is appreciated that variations and modifications may be made without departing from the spirit of the invention.

We claim:

1. A method utilizing signal-processed ECG and heart-sound signal information for assessing a pacemaker patient's hemodynamic condition comprising
    collecting, over a selected time span, for transmission for hemodynamic-condition signal processing, simultaneous ECG-electrical and heart-sound acoustic signals,
    while so collecting, detecting, electrically, pacemaker-induced ventricular stimulation,
    on detecting such stimulation, creating and applying a selected blanking time which effectively prevents hemodynamic-condition signal-processing of acoustic signals that are collected during that blanking time, and
    generating, at the beginning of the created and applied blanking time, an acoustic window which permits examining, during that window, of any collected and thus windowed acoustic signal to determine whether it represents an acoustic artifact produced by pacemaker-induced phrenic nerve stimulation.

2. The method of claim 1 which further comprises selectively using the determination of the presence of phrenic nerve stimulation to modify the operation of the patient's pacemaker.

3. The method of claim 1 which further comprises, in relation to application of a blanking time, producing a time-based graphical display containing indicia which are visually descriptive of selective components of the patient's hemodynamic condition.

4. The method of claim 3, wherein said producing includes establishing (a) an ECG-signal display component, (b) a heart-sound acoustic signal display component, and (c) an intuitive, heart-sound marker display component designating the time locations of at least one of heart sounds $S_1, S_2, S_3$ and $S_4$.

5. The method of claim 3, wherein said producing includes establishing an intuitive heart-sound marker display designating the time locations of at least one of heart sounds $S_1, S_2, S_3$ and $S_4$.

6. The method of claim 4, wherein said establishing of an intuitive heart-sound marker display includes placing therein (a) systolically-associated sound markers which are presented above a neutral axis line, and (b) diastolically-associated sound markers which are displayed below the same neutral axis line.

7. The method of claim 6, wherein said producing of a display presenting hemodynamic condition information involves including in that display elements relating to (a) electromechanical activation time, (b) LV systolic time, (c) pre-atrial diastolic time, and (d) accelerated atrial filling time.

8. The method of claim 1 which further comprises utilizing collected ECG-electrical and heart-sound acoustic signals in a feedback manner to effect changes in the operation of the patient's pacemaker in a fashion aimed at improving the patient's hemodynamic status.

* * * * *